United States Patent
Shreeve et al.

(10) Patent No.: US 6,215,021 B1
(45) Date of Patent: Apr. 10, 2001

(54) TRIFLUOROMETHYLATING REAGENTS AND SYNTHESIZING PROCESSES

(75) Inventors: Jean'ne M. Shreeve, Moscow, ID (US); Jing-Jing Yang, Winter Haven, FL (US); Robert L. Kirchmeier, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

(21) Appl. No.: 09/335,857

(22) Filed: Jun. 17, 1999

Related U.S. Application Data

(60) Provisional application No. 60/089,577, filed on Jun. 17, 1998.

(51) Int. Cl.$^7$ .................................................. C07C 309/00
(52) U.S. Cl. .................................................. 562/30
(58) Field of Search ................................. 562/30

(56) References Cited

U.S. PATENT DOCUMENTS

| | | | |
|---|---|---|---|
| 4,808,748 | 2/1989 | Lin et al. | 558/378 |
| 4,814,480 | 3/1989 | Davidson | 558/378 |
| 4,814,482 | 3/1989 | Davidson | 558/378 |
| 4,822,904 | 4/1989 | Davidson | 558/378 |
| 5,475,165 | 12/1995 | Palmer et al. | 570/144 |
| 5,817,830 | 10/1998 | Therien et al. | 548/400 |

OTHER PUBLICATIONS

Yang et al, "New Electrophilic Trifluoromethylating Agents" in J. Org. Chem. 1998, 63, 2656–2660.*
Umemoto, Teruo, "Electrophilic Perfluoroalkylating Agents," Chemical Reviews, Jul./Aug. 1996, vol. 96, No. 5, pp. 1757–1777.
Umemoto, Teruo et al., "Power–Variable Trifluofomethylating Agents, (Trifluoromethyl) Dibenzothio–and–Selenophenium Salt System," Tetrahedron Letters, 1990, vol. 31, No. 25, pp. 3579–3582.
Umemoto, Teruo et al., "Power–Variable Electrohilic Trifluoromethylating Agents. S–, Se–, and Te–(Trifluoromethyl) dibenzothio–, seleno–, and –tellurophenium Salt System," J. Am. Chem. Soc., 1993, vol. 115, No. 6, pp. 2156–2164.

* cited by examiner

Primary Examiner—Ralph Gitomer
Assistant Examiner—D Khare
(74) Attorney, Agent, or Firm—Ormiston & McKinney, PLLC

(57) ABSTRACT

A family of electrophilic trifluoromethylating reagents which can be synthesized by comparatively simple, inexpensive routes, and for which the reactivity can be varied according to need. A composition of matter according to the first embodiment of the invention comprises a compound having the formula:

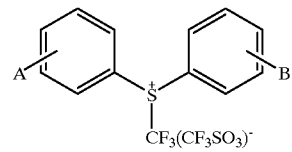

in which A comprises H or F and B comprises F, $SCF_3$, $OCF_3$, $OCHF_2$, $S^+(CF_3)C_6H_5$, $NO_2$ or an $NO_2$ substituent. In a second embodiment of the invention, a process for preparing a trifluoromethyl diphenylsulfonium triflate compound corresponding to the formula shown above comprises reacting phenyl trifluoromethyl sulfoxide or one of its derivatives with an aromatic compound in which A comprises H or F and B comprises H, F, $SCF_3$, $OCF_3$, $OCHF_2$, $S^+(CF_3)C_6H_5$, $NO_2$ or an $NO_2$ substituent. In a third embodiment of the invention, a trifluoromethylation process comprises reacting a trifluoromethyl diphenylsulfonium triflate corresponding to the formula shown above with an electron rich substrate.

19 Claims, No Drawings

TRIFLUOROMETHYLATING REAGENTS AND SYNTHESIZING PROCESSES

CROSS REFERENCE TO RELATED APPLICATION

This application claims subject matter disclosed in the copending provisional application Ser. No. 60/089,577 filed Jun. 17, 1998 entitled Trifluoromethyl Transferring Reagents, which is incorporated herein by reference in its entirety.

GOVERNMENT RIGHTS

Research leading to this invention was supported in part by a grant from the United States National Science Foundation under grants EPS-9350539 and CHE-9720635. The United States Government has certain rights in the invention.

FIELD OF THE INVENTION

This invention relates to the transfer of a trifluoromethyl group to a desired substrate molecule and the formation of trifluoromethylating reagents. More particularly, the invention relates to trifluoromethyl derivatives of electron rich aromatic, heteroaromatic, and nonaromatic substrates.

BACKGROUND

The trifluoromethyl group ($CF_3$) is an important structural moiety in diverse classes of bioactive organic molecules. The $CF_3$ group has a bigger van der Waals radius than that of a $CH_3$ group and the same electronegativity as oxygen (Table 1).

The C—F bond in trifluoromethylated compounds results in added stability and lipophilicity of the molecule. As a consequence, the introduction of a trifluoromethyl group into organic molecules often changes their physical, chemical, and physiological properties. Compounds containing the trifluoromethyl group are found in a variety of commercially important dyes, polymers, pharmaceuticals, and agrochemicals. The dye industry has found that trifluoromethylated chromophores exhibit increased light fastness compared with the nonfluorinated compounds. Trifluoromethylated polymers have high thermal stability and enhanced mechanical and electrical properties. Many

TABLE 1 van der Waals radius and electronegativity of different groups

| Group/atom | van der Waals radius (Å) | Group/atom | Electronegativity |
|---|---|---|---|
| $CF_3$ | 2.7 | $CF_3$ | 3.5 |
| $CH_3$ | 2.0 | $CH_3$ | 2.3 |
| $CCl_3$ | 3.5 | C | 2.5 |
| F | 1.4 | F | 4.0 |
| H | 1.2 | H | 2.1 |
| O | 1.5 | O | 3.5 |
|  |  | Cl | 3.0 | of these polyfluorinated polymers find application as liquid crystals. In a wide variety of agrichemicals and pharmaceuticals, the properties of the trifluoromethyl group, i.e., to increase lipophilicity and to act as an inhibitor of enzyme action, are key reasons for incorporation. Thus, a variety of reagents have been developed in order to introduce the $CF_3$ group into organic molecules. Currently, there are three available methods for directly introducing a $CF_3$ group into target compounds: (i) organometallic based on $CF_3Cu$, (ii) nucleophilic based on $CF_3SiMe_3$, and (iii) electrophilic based on S-(trifluoromethyl) dibenzothiophenium triflate.

By nucleophilic and electrophilic are meant techniques or reagents that will transfer a $CF_3$ group to an electron-deficient or electron-rich portion, respectively, of the target molecule. Organic molecules, while retaining electrical neutrality, will often show a partial separation of charge on their constituent atoms, especially due to the effect of electron-withdrawing or electron donating substituents. Aromatic rings and double and triple bonds are typical electron-rich environments. The presence of electron withdrawing substituents such as $F^-$, $Cl^-$, $NO_2^-$, $N(SO_2CF_3)^-$, $N(SO_2F)_2^-$, $CN^-$ can produce electron-deficient regions in molecules.

The introduction of a $CF_3$ group into an electron rich environment is becoming more and more important in organic and bioorganic synthesis. It is not a trivial task, however. It is extremely difficult to generate the $CF_3$ cation chemically, due to its high electronegativity (3.45). In 1984, Yagupol'skii reported two trifluoromethyl sulfonium salts, trifluormethyl-p-chlorophenyl(2,4-dimethylphenyl)sulfonium hexafluoroantimonate (1) and trifluoromethyl-p-chlorophenyl-p-anisylsulfonium hexafluoroantimonate (2), that were capable of acting as trifluoromethylating reagents. Yagupol'skii, L. M.; Kondratenko, N. Y.; Timofeeva, G. N. *Zh. Org. Khim.* 1984, 20, 115; *Chem. Abstr.* 1984, 100, 191494e. Compounds 1 and 2 react with sodium p-nitrothiophenolate in DMF to give p-nitrophenyl trifluoromethyl sulfide in high yield. However, 1 and 2 were synthesized from the extremely hygroscopic intermediate fluoro(trifluoromethyl)-p-chlorophenylsulfonium hexafluoroantimonate. Both products, 1 and 2, are also extremely hygroscopic. Furthermore, they are unreactive with the highly activated aromatic compound N,N-dimethylaniline.

In 1990, Umemoto reported power-variable electrophilic trifluoromethylating reagents (FIG. 1) that can transfer the $CF_3$ group to different kinds of organic molecules. Umemoto, T.; Ishihara, S. *Tetrahedron Lett.* 1990, 31, 3579; Umemoto, T.; Ishihara, S. *J. Am. Chem. Soc.* 1993, 115, 2156. They react readily with strongly activated aromatic systems, e.g. N,N-dimethylaniline. Although these reagents are very useful, they are prepared by using multistep, inconvenient synthetic routes that require gaseous CF3I or CF3Br for the triflouromethylation reaction. These reagents, although available commercially, are expensive.

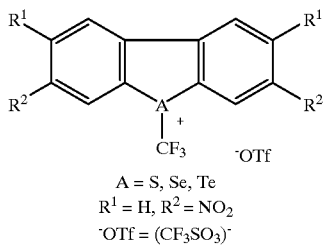

FIG. 1

A = S, Se, Te
$R^1$ = H, $R^2$ = $NO_2$
$^-OTf$ = $(CF_3SO_3)^-$

Umemoto also described several other trifluoromethylating reagents with varying power to transfer the $CF_3$ group, which are shown in FIG. 2. The synthesis of these reagents was described as time consuming, and in some cases the yields were poor. Umemoto, T. *Chem. Rev.* 1996, 96, 1757–77.

FIG. 2

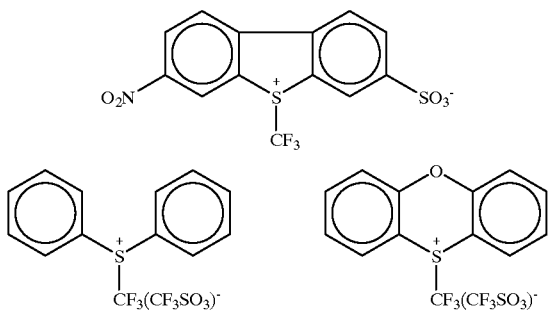

There is an evident need for trifluoromethylating reagents which can be synthesized by straightforward, economical, efficient methods, and which are stable and easy to handle, and which will transfer the $CF_3$ group in good yield to a wide variety of target molecules that have electron-rich centers.

SUMMARY OF THE INVENTION

Accordingly, it is one objective of this invention to provide a family of electrophilic trifluoromethylating reagents which can be synthesized by comparatively simple, inexpensive routes, and for which the reactivity can be varied according to need. By triflates is meant salts of the triflate anion $(CF_3SO_3)^-$. The invention may be embodied in new trifluoromethyl diphenylsulfonium triflate compounds having the structure shown in FIG. 3 (referred to as the first embodiment), processes for making trifluoromethyl diphenylsulfonium triflate compounds (referred to as the second embodiment), and trifluoromethylation processes in which a trifluoromethyl group may be transfered to a desired substrate molecule (referred to as the third embodiment).

FIG. 3

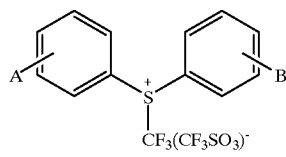

A composition of matter according to the first embodiment of the invention comprises a compound having the formula:

in which A comprises H or F and B comprises F, $SCF_3$, $OCF_3$, $OCHF_2$, $S^+(CF_3)C_6H_5$, $NO_2$ or an $NO_2$ substituent. In another aspect of this embodiment, A comprises F and B comprises H in the above formula.

In a second embodiment of the invention, a process for preparing trifluoromethyl diphenylsulfonium triflate compounds corresponding to the formula:

comprises reacting phenyl trifluoromethyl sulfoxide or one of its derivatives with an aromatic compound in which A comprises H or F and B comprises H, F, $SCF_3$, $OCF_3$, $OCHF_2$, $S^+(CF_3)C_6H_5$, $NO_2$ or an $NO_2$ substituent.

In a third embodiment of the invention, a trifluoromethylation process comprises reacting a trifluoromethyl diphenylsulfonium triflate compound corresponding to the formula:

with an electron rich substrate.

DETAILED DESCRIPTION

A. Preparation of Trifluoromethylating Reagents

Abbreviations used:

IR Infrared spectroscopy;

NMR Nuclear magnetic resonance spectroscopy;

EI-MS Electron Impact Mass spectroscopy; and

FAB$^+$-MS Fast Atom Bombardment Mass spectroscopy.

Structures for intermediates and trifluoromethylating reagents were determined and confirmed by some or all of the following analytical techniques, as is well known in the art: IR spectroscopy; $^1$H-, $^{13}$C- and $^{19}$F-NMR spectroscopy; EI- and FAB$^+$ mass spectroscopy; and chemical analysis.

$^{19}$F, $^1$H and $^{13}$C NMR spectra were obtained with a 200 MHZ NMR spectrometer using $CDCl_3$ as solvent unless otherwise indicated. Chemical shifts are reported with respect to $(CH_3)_4Si$ or $CFCl_3$. Products were separated by column chromatography with 70–230 mesh silica gel.

EXAMPLE 1

Preparation of Phenyl Trifluoromethyl Sulfoxide (5) and Phenyl Trifluoromethyl Sulfone (6), Intermediates used in the Synthesis of Trifluoromethylating Reagents Trifluoromethylthiocopper(I) (3) was prepared by reacting silver fluoride (I) and carbon disulfide in acetonitrile, followed by a metathetical reaction with copper (I) bromide. The white solid 3 was obtained in high yield (98%) and was reacted with iodobenzene in N-methylpyrrolidone (NMP) to give phenyl trifluoromethyl sulfide (4) in 65% yield. When this reaction was carried out in a different solvent, e.g. in DMF, the yield was not improved. The product was purified by column chromatography. The $^{19}$F NMR spectrum of 4 consisted of a single resonance at −43.0 ppm in $CDCl_3$. Phenyl trifluoromethyl sulfoxide (5) was obtained from the oxidation of phenyl trifluoromethyl sulfide (4) with m-chloroperbenzoic acid via reaction overnight at 0° C. in $CH_2Cl_2$. This oxidation reaction is very sensitive to temperature. If the temperature exceeded 0° C., the yield of sulfone (6) was enhanced. For example, when the reaction was carried out at room temperature for 12 h, the ratio of 5:6 was 5:2. On the other hand at 0° C. for 10 h, the ratio of 5:6 was 95:2. Compounds 5 and 6 were separated by column chromatography. These reactions are shown in FIG. 4.

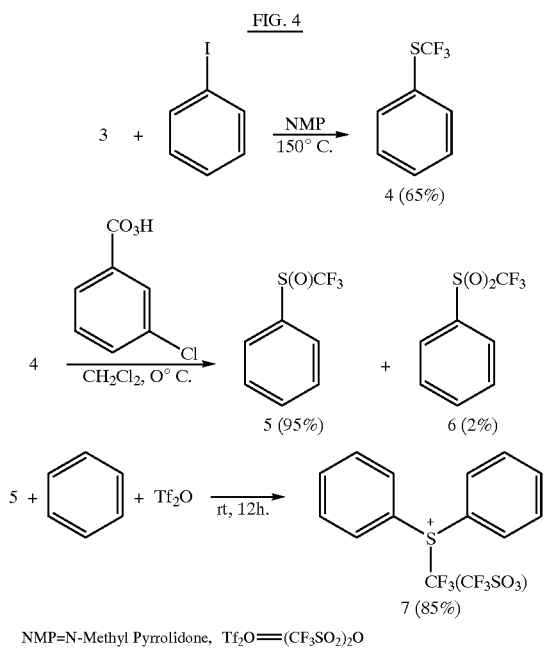

NMP=N-Methyl Pyrrolidone, Tf$_2$O≡(CF$_3$SO$_2$)$_2$O

Synthetic details: To a stirred solution of phenyl trifluoromethyl sulfide (1.0 g, 5.6 mmol) in dry CH$_2$Cl$_2$ (40 mL) at 0° C. under N$_2$ was added m-chloroperbenzoic acid (1.46 g, 7.3 mmol) in small portions. After the reaction mixture was stirred for 10 h at 0° C., and then rt for 1 h, the solution was filtered and evaporated. The residue was subjected to silica gel column chromatography using a mixture of ethyl acetate and hexanes (30:1) as eluent to give product 5 (1.035 g, 95%). Structure determination: IR (film): 3067 (w), 2359 (w), 1448 (m), 1370 (m), 1191 (s), 1141 (s), 1089 (s), 688 (m), 606 (m) cm$^{-1}$; $^1$H-NMR (CDCl$_3$): 7.54–8.06 (m, 5H); $^{19}$F NMR (CDCl$_3$): −74.9 (s); $^{13}$C NMR (CDCl$_3$): 134, 131, 130, 126, 121 (q, J=260 Hz) ppm; EI-MS [m/e (species, intensity)]: 194 (M$^+$, 4.8), 141 (M$^+$-C$_4$H$_5$, 13), 125 (M$^+$-CF$_3$, 100), 109 (M$^+$-CF$_3$-O, 8), 77 (C$_6$H$_5$, 65), 69 (CF$_3$, 7.2). Similarly phenyl trifluoromethyl sulfone (6) (21.8 mg, 2%) was eluted, and the structure confirmed: IR (film): 3070 (w), 1585 (w), 1451 (m), 1370 (s), 1221 (s), 1143 (s), 1075 (m), 605 (m), 576 (m) cm$^{-1}$; $^1$H NMR (CDCl$_3$): 8.04 (bd, J$_{23}$=11.2 Hz, 2H), 7.84 (dt, J$_{43}$=8.0 Hz, J$_{42}$=2.0 Hz, 1H), 7.63 (dt, J$_{32}$=8.0 Hz, J$_{34}$8.0 Hz, 2H); $^{19}$F NMR (CDCl$_3$): −78.8 (s, 3F); $^{13}$C NMR (CDCl$_3$): 137, 131, 130, 129, 124 (q, J=261 Hz) ppm; EI-MS [m/e (species, intensity)]: 210 (M$^+$, 2.7), 141 (M$^+$-CF$_3$, 44.8), 125 (M$^+$-CF$_3$-O, 2.9), 77 (C$_6$H$_5^+$, 100), 69 (CF$_3^+$, 2.9).

EXAMPLE 2

Preparation of S-(trifluoromethyl)diphenylsulfonium Triflate (7)

S-(Trifluoromethyl)diphenylsulfonium triflate (7) and its derivatives were obtained by an intermolecular condensation reaction of phenyl trifluoromethyl sulfoxide 5 with benzene, 1-fluorobenzene, 1,3-difluorobenzene, 1-trifluoromethoxybenzene or α,α-difluoroanisole by the action of triflic (trifluoromethanesulfonic) anhydride at room temperature. This reaction is shown in FIG. 5. The products were easily purified by column chromatography and recrystallization. Compound 7 was obtained in a yield of 85%. A parent ion for 7 appears in the mass spectrum at m/z 255 (FAB-MS).

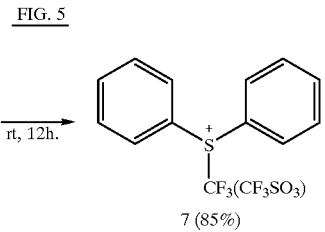

Synthetic details: To a solution of phenyl trifluoromethyl sulfoxide (5) (194.17 mg, 1.0 mmol) in dry benzene (2.6 mL, 30 mmol) was added (CF$_3$SO$_2$)$_2$O (0.84 mL, 5.0 mmol) at 0° C. The resulting solution was stirred for 1 h at 0° C. and then rt for another 24 h. The solvent was evaporated and the residue was purified by column chromatography on silica gel with CH$_3$CN—CH$_2$Cl$_2$ (1:4) as eluent. The product was obtained as a white crystal (343.4 mg, 85%), m. p. 84–5 C (recrystallized from ethyl acetate/hexanes). IR (nujol): 3115 (w), 1263 (s), 1224 (s), 1146 (s), 1083 (s), 513 (s) cm$^{-1}$; $^1$H NMR (CDCl$_3$): 8.15 (d, J$_{23}$=7.6 Hz, 4H), 7.82 (m, 6H); $^{19}$F NMR (CDCl$_3$): −49.6 (s, 3F), −78.6 (s, 3F); $^{13}$C NMR (CDCl$_3$): 137, 133, 132, 127 (q, J=252 Hz), 122 (q, J=253 Hz), 117 ppm; FAB$^+$-MS [m/e (species, intensity)]: 255 ((C$_{13}$H$_{10}$F$_3$S)$^+$, 100), 186 ((C$_{13}$H$_{10}$F$_3$S)$^+$-CF$_3$, 81.2), 178 ((C$_{13}$H$_{10}$F$_3$S)$^+$-C$_6$H$_5$, 2.1), 109 ((C$_{13}$H$_{10}$F$_3$S)$^+$-C$_6$F$_5$ -CF$_3$, 14.6); Chemical Analysis: Calculated for C$_{14}$H$_{10}$F$_6$O$_3$S$_2$: C, 41.58; H, 2.49; F, 28.22. Found: C, 41.62; H, 2.57; F, 28.60.

The intermolecular condensation reaction of phenyl trifluoromethyl sulfoxide (5) with benzene induced by Tf$_2$O apparently proceeds via an intermediate designated (A) in FIG. 6. This is also consistent with the fact that electron-withdrawing groups on the benzene ring reduced its reactivity with the sulfoxide.

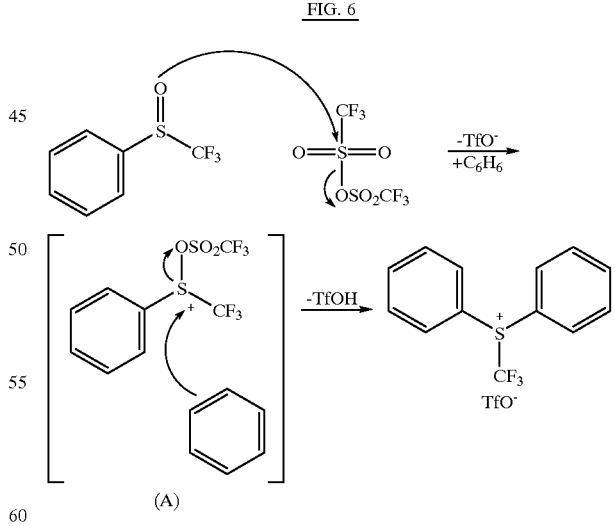

EXAMPLE 3

Preparation of S-(trifluoromethyl)phenyl-4-fluorophenylsulfonium Triflate (8)

When 1-fluorobenzene was reacted with phenyl trifluoromethyl sulfoxide, we expected two major products, the ortho- and para-substituted isomers. Surprisingly, however, the para-isomer of 8 was obtained in a yield of 76%. The structure of 8 was confirmed based on their $^1$H and $^{19}$F NMR and mass spectra. The FAB-MS showed a parent ion at m/z 273 In the $^1$H NMR spectrum, H2 and H6 gave peaks that are a doublet of doublets, with coupling constants of $J_{23'}$=6.0 Hz and $J_{2F}$=4.0 Hz. Protons H3 and H5 resonate as another set of doublet of doublets, $J_{32}$=6.0 Hz and $J_{3F}$=9.0 Hz. These two types of protons confirm that the F atom is at the para-position. If the F atom were located at the ortho-position or the meta-position, the $^1$H NMR would show four types of protons and much more complex fine coupling. The synthesis of 8 is shown in FIG. 7.

FIG. 7

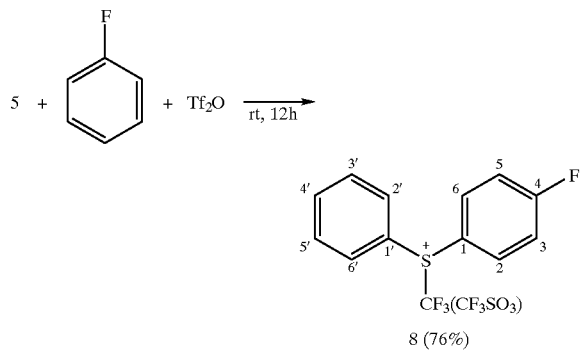

8 (76%)

Synthetic details: To a solution of phenyl trifluoromethyl sulfoxide (5) (582 mg, 3.0 mmol) in dry 1-fluorobenzene (8.4 mL, 30 mmol) was added $(CF_3SO_2)_2O$ (2.5 mL, 15 mmol) at 0° C. The reaction mixture was stirred for 10 h at 0° C., and then at rt for another 2 h. Removal of the solvent left a crude residue that was subjected to column chromatography on silica gel using $CH_3CN$—$CH_2Cl_2$ (1:4) as eluent to give the product as white crystals (886 mg, 70%), mp 80–1 C (recrystallized from ethyl acetate/hexanes). IR (nujol): 3108 (m), 1719 (w), 1589 (m), 1494 (m), 1255 (s), 1171 (s), 640 (s) cm$^{-1}$; $^1$H NMR (CDCl$_3$): 8.35 (dd, $J_{23}$=6.0 Hz, $J_{2F}$=4.0 Hz, 2H), 8.19 (bd, $J_{2'3'}$=6.0 Hz, 2H), 7.83 (m, 3H), 7.51 (dd, $J_{32}$=6.0 Hz, $J_{3F}$=9.0 Hz, 2H); $^{19}$F NMR (CDCl$_3$): −50.7 (s, 3F), −78.7 (s, 3F), −95.5 (s, 1F); $^{13}$C NMR (CDCl$_3$): 170 (d, J=261 Hz), 139, 137, 135, 135, 127 (q, J=265 Hz), 126 (q, J=263 Hz), 121, 116 ppm; FAB$^+$-MS [m/e (species, intensity)]: 273 (($Cl_3H_9F_4S$)$^+$, 100), 272 (($C_{13}H_8F_4S$)$^+$, 14.2), 254 (($C_{13}H_9F_3S$)$^+$, 5.9), 204 (($C_{13}H_9F_4S$)$^+$-CF$_3$, 98.0), 196 (($C_{13}H_9F_4S$)$^+$-C$_6$H$_5$, 5.3), 178 (($C_{13}H_9F_4S$)$^+$-C$_6$H$_4$F, 3.4), 127 (($C_6H_4FS$)$^+$, 13.0), 109 (($C_6H_5S$)$^+$, 20.1) ); Chemical analysis: Calculated for $C_{14}H_9F_7O_3S_2$: C, 39.81; H, 2.15. Found: C, 39.45; H, 2.17.

EXAMPLE 4

Preparation of S-(trifluoromethyl)phenyl-2,4-difluorophenylsulfonium Triflate (9)

We also expected both ortho- and para-substituted isomers from the reaction of 1,3-difluorobenzene with phenyl trifluoromethyl sulfoxide (5). However, as was the case with 1-fluorobenzene, we surprisingly obtained the para-isomer of 9 in a yield of 70%. For compound 9, the $^{19}$F NMR spectrum showed two types of fluorine atoms on the benzene ring. One gave rise to a resonance at −91.74 ppm and the second at −98.22 ppm. The $^1$H NMR spectrum showed a resonance at 7.90 ppm for H6, as a broad doublet $J_{65}$=7.5 Hz. H5 is at 7.45 ppm as a doublet of doublets with coupling constants of $J_{56}$=8.10 Hz, $J_{54F}$=7.8 Hz. Proton H3 is at 7.25 ppm, and is also a doublet of doublets with coupling constants of $J_{32F}$=9.0 Hz, $J_{34F}$=9.0 Hz. There are three different types of protons on the fluorinated benzene ring, confirming the structure of 9 as shown. The FAB-MS shows a parent ion for 9 at m/z 291. This reaction is shown in FIG. 8.

FIG. 8

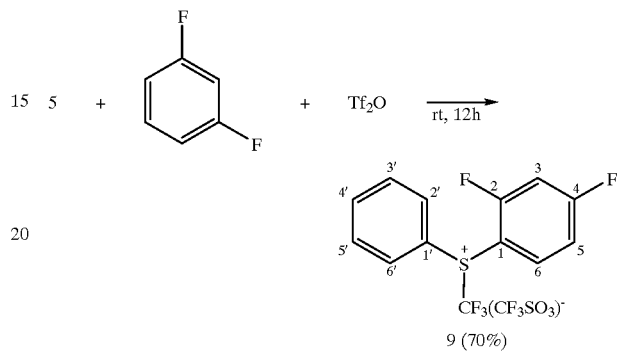

9 (70%)

Synthetic details: To a solution of phenyl trifluoromethyl sulfoxide (5) (485 mg, 2.5 mmol) in dry 1,3-difluorobenzene (7.4 mL, 75 mmol) was added $(CF_3SO_2)_2O$ (2.10 mL, 12.5 mmol) at 0° C. The reaction mixture was stirred for 2 h at 0° C., and then at rt for another 20 h. The solvent was evaporated under reduced pressure and the residue was purified by column chromatography on silica gel using $CH_3CN$—$CH_2Cl_2$ (1:4) as eluent. The product was obtained as a white crystal (770 mg, 70%), m. p. 78–9° C. (recrystallized from ethyl acetate/hexanes). IR (nujol): 3099 (s), 1600 (s), 1479 (s), 1450 (s), 1200 (s) (cm$^{-1}$); $^1$H NMR (CDCl$_3$): 8.26 (d, $J_{2'3'}$=8.1 Hz, $J_{4'3'}$=8.1 Hz, 3H), 7.90 (bd, $J_{65}$7.5 Hz, 1H), 7.75 (dd, $J_{3'2'}$=7.8 Hz, $J_{3'4'}$=7.8 Hz, 2H), 7.45 (dd, $J_{56}$=8.1 Hz, $J_{54F}$=7.8 Hz, 1H), 7.25 (dd, $J_{32F}$=9.0 Hz, $J_{34F}$=9.0 Hz, 1H); $^{19}$F NMR (CDCl$_3$): −47.6 (s, 3F), −78.3 (s, 3F), −91.7 (s, 1F), −98.2 (s, 1F); $^{13}$C NMR (CDCl$_3$): 168 (d, J=261 Hz), 163 (d, J=262), 138, 137, 133, 132, 126 (q, J=262), 123 (q, J=262 Hz), 120, 117, 115, 108 ppm; FAB$^+$-MS [m/e (species, intensity)]: 291 (($C_{13}H_8F_5S$)$^+$, 100), 222 (($C_{13}H_8F_5S$)$^+$-CF$_3$, 80.6), 145 (($C_{13}H_8F_5S$)$^+$-C$_6$H$_5$-CF$_3$, 15.0) ); Chemical analysis: Calculated for $C_{14}H_8F_8O_3S_2$: C, 38.18; H, 1.83; F, 34.52. Found: C, 37.97; H, 1.88; F, 34.90.

The results obtained from the reactions of 5 with 1-fluorobenzene and 1,3-difluorobenzene show that steric factors are important with respect to the isomer formed. When either the group on the ring or the attacking group is large, steric hindrance inhibits the formation of the ortho-product, and the amount of para-isomer obtained is increased.

EXAMPLE 5

Preparation of S-(trifluoromethyl)phenyl-4-trifluoromethoxyphenylsulfonium Triflate (10) and S-(trifluoromethyl)phenyl-4-difluoromethoxyphenylsulfonium Triflate (11)

When 5 was reacted with 1-trifluoromethoxybenzene or α,α-difluoroanisole in the presence of trifluoromethane sulfonic anhydride at room temperature, compounds (10) and (11), respectively, were formed as shown in FIG. 9. The products were easily purified by column chromatography and recrystallization. A parent ion for 10 appeared in the mass spectrum at m/z 339 (FAB-MS) and for 11 at m/z 321 (FAB-MS). The structures of both the products were confirmed by their $^1$H and $^{19}$F NMR spectra. In the $^1$H NMR spectrum H2 and H6 gave peaks that are doublets, with coupling constants of $J_{23}$=8.96 Hz. Protons H3 and H5 resonate as another set of doublets, $J_{32}$=8.83 Hz. These two types of protons confirmed that the OCF$_3$ group is at the para-position. If the OCF$_3$ groups were located at the ortho-position or the meta-position, the $^1$H NMR spectrum would show four types of protons and much more complex fine coupling. Based on the same facts for compound 11, the structure of 11 was confirmed with the OCHF$_2$ group at the para-position. From these results, it is seen that steric factors are important with respect to the isomer formed. When either the group on the ring or the attacking group is large, steric hindrance inhibits the formation of the ortho-product, and amount of the para-isomer obtained is increased. These reactions are shown in FIG. 9.

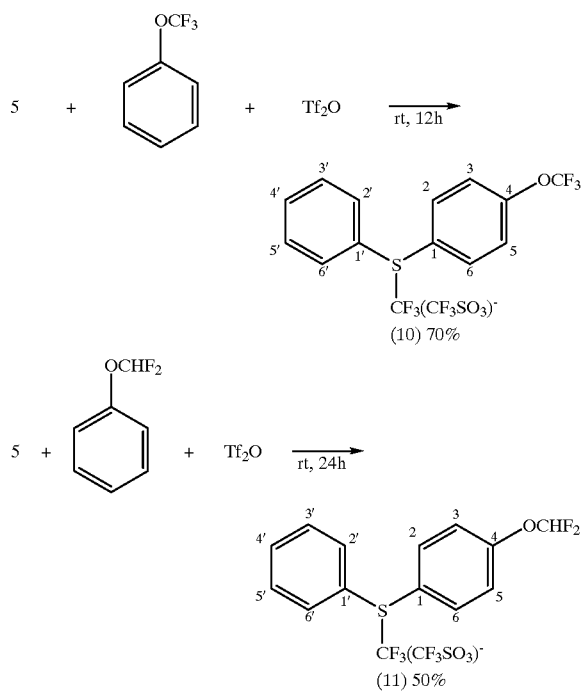

FIG. 9

Synthetic details-S-(Trifluoromethyl)phenyl-4-trifluoromethoxyphenylsulfonium triflate (10): To a solution of phenyl trifluoromethyl sulfoxide (500 mg, 2.58 mmol) in dry trifluoromethoxybenzene (2.0 mL, 15.13 mmol) was added Tf$_2$O (2.0 mL, 11.89 mmol) at 0° C. The resulting solution was stirred for 24 hour at rt. The solution was evaporated then purified by column chromatography on silica gel using CH$_3$CN—CH$_2$Cl$_2$ (1:4, 1:1) as eluent. The product was recrystallized from CH$_2$Cl$_2$—CH$_3$CN (4:1) as a white crystal (881 mg, 70%) mp 77–8° C. IR (nujol): 3010 (m), 1491 (m), 1450 (m), 1276 (s), 1100(s), 688 (s) (cm$^{-1}$); $^1$H NMR (CDCl$_3$): 8.27 (d, $J_{23}$=8.96 Hz, H2, H6, 2H), 8.14 (d, $J_{2'3'}$=7.95 Hz, H2', H6', 2H), 7.88 (m, H3', H4' and H5', 3H), 7.60 (d, $J_{32}$=8.83 Hz, H3 and H5, 2H); $^{19}$F NMR (CDCl$_3$) −50.36 (s, SCF$_3$, 3F), −57.98 (s, OCF$_3$, 3F), −78.29 (s, CF$_3$SO$_3$, 3F); $^{13}$C NMR (CDCl$_3$), 155.32 (4), 149.21 (q, J=251.12Hz, CF$_3$SO$_3$), 137.27, 135.52, 132.90, 132.89, 126.43 (q, J=276.22 Hz, SCF$_3$), 123.10, 119.90 (q, J=263.72 Hz, OCF$_3$), 116.69, 114.21 ppm; FAB-MS m/e (species, %) 339 (M$^+$, 100), 270 (M$^+$-CF$_3$, 48).

Synthetic details-S-(Trifluoromethyl) phenyl-4-difluoromethoxyphenylsulfonium triflate (11): To a solution of phenyl trifluoromethyl sulfoxide (500 mg, 2.58 mmol) in dry α,α-difluoroanisole (2.0 mL, 16.65 mmol) was added Tf$_2$O (2.0 mL, 11.89 mmol) at 0° C. The resulting solution was stirred for 24 hour at r t. The solution was evaporated then purified by column chromatography on silica gel using a CH$_3$CN—CH$_2$Cl$_2$ (1:4, 1:1) as eluent. The product was recrystallized from CH$_2$Cl$_2$:CH$_3$CN (4:1) as white crystals. (606 mg, 50%). mp. 80–1° C. IR (nujol): 3100 (w), 1581 (m), 1498 (m), 1350 (s), 1100 (s), 640 (s) (cm$^{-1}$); $^1$H NMR (CDCl$_3$): 8.25 (d, $J_{23}$=12.21 Hz, H2, H6, 2H), 8.14 (d, $J_{2'3'}$=7.80 Hz, H2' and H6', 2H), 7.80 (m, H3', H4' and H5', 3H), 7.50 (d, $J_{32}$=12.21 Hz, H3 and H5, 2H), 6.80 (t, H=71.65 Hz, CHF$_2$, 1H); $^{19}$F NMR (CDCl$_3$) −50.79 (s, SCF$_3$, 3F), −78.81 (s, CF$_3$SO$_3$, 3F), −84.60 (d, J=71.612 Hz, OCHF$_3$, 2F); $^{13}$C NMR (CDCl$_3$), 162.31 (q, J=251.12 Hz, CF$_3$SO$_3$), 157.97, 137.14, 135.70, 132.57, 132.29, 126.34(q, J=219.73, SCF$_3$), 121.70, 120.14 (dt, J=250.11), 117.45, 110.98ppm; FAB-MS m/e (species, %) 321 (M$^+$, 100), 251 (M$^+$-CF$_3$, 46).

EXAMPLE 6

Preparation of S-(trifluoromethyl)phenyl-3-nitrophenylsulfonium Triflate (12) and S-(trifluoromethyl)-4-fluorophenyl-3-nitrophenylsulfonium Triflate (13)

The reactivity of the S-(trifluoromethyl) diphenylsulfonium triflate salt can be modified by the introduction of different substituents into the ring. Mononitrated thiophenium salts were prepared from the reaction of 7 or 8 with a mixture of fuming HNO$_3$ and concentrated H$_2$SO$_4$at 80° C. as shown in FIG. 10. Products 12 and 13 were purified by recrystallization. When 7 and 8 were nitrated, the meta-substituted products were expected since CF$_3$S$^+$ is a meta-directing group. Compounds 12 and 13 were obtained in yields of 75% and 70%, respectively. The structures of 12 and 13 were elucidated by NMR and MS spectral analysis. For compound 12, FAB-MS shows a parent ion at m/z 300. The $^1$H NMR spectrum shows H2 at 8.83 ppm as a doublet of doublets with coupling constants of $J_{24}$=$J_{26}$=2.0 Hz. Proton H4 resonates at 8.75 ppm as a doublet of doublets of doublets, with coupling constants of $J_{45}$=6.0 Hz and $J_{42}$=$J_{46}$=2.0 Hz. Proton H6 is found at 8.42 ppm, as a multiplet, with one measurable coupling constant of $J_{65}$=6.0 Hz. The other six hydrogen atoms appear as two multiplets at 8.15 and 7.90 ppm. The presence of four different types of protons and their fine structure in the NMR spectra confirmed the structure of 12. For compound 13, the FAB-MS spectrum shows a parent ion at m/z 318. The $^1$H NMR shows H2' at 8.81 ppm as a doublet of doublets with coupling constants of $J_{2'4'}$=$J_{2'6'}$=2.0 Hz. Proton H4' is at 8.73 ppm as a doublet of doublets of doublets with coupling constants of $J_{4'5'}$=6.0 Hz, $J_{4'2'}$=$J_{4'6'}$=2.0 Hz. Proton H5' is found at 8.10 ppm as a doublet of doublets with coupling constants of $J_{5'4'}$=J5'6'=8.0 Hz, while a complex multiplet at 8.42 ppm was assigned to H6'. One measurable coupling constant is $J_{6'5'}$=8.0 Hz. For H2 and H6 at 8.24 ppm, a doublet of doublets resonance is seen and the coupling constants are $J_{23}$=8.0 Hz and $J_{2F}$=8.0 Hz. H3 and H5 are at 7.67 ppm also as a doublet of doublets with coupling constants of $J_{32}$=8.0 Hz, $J_{3F}$=8.1 Hz. These data are consistent with the presence of a single NO$_2$ group on the nonfluorinated benzene ring. Only two types of protons are present on the benzene ring that contains a fluorine atom. The other four types of protons and their coupling constants confirm the fact that the $NO_2$ group is at the meta-position of the nonfluorinated benzene ring. When 8 was nitrated, the nitro group was not incorporated into the fluorobenzene ring under the reaction conditions used. Only the nonfluorinated benzene ring could be nitrated. The electrophilic nitration reaction becomes more difficult when more fluoro groups are on the benzene ring. For example, the compound S-(trifluoromethyl)phenyl-2,4-difluorophenylsulfonium triflate (9) was examined, and nitration did not occur under any of the reaction conditions employed.

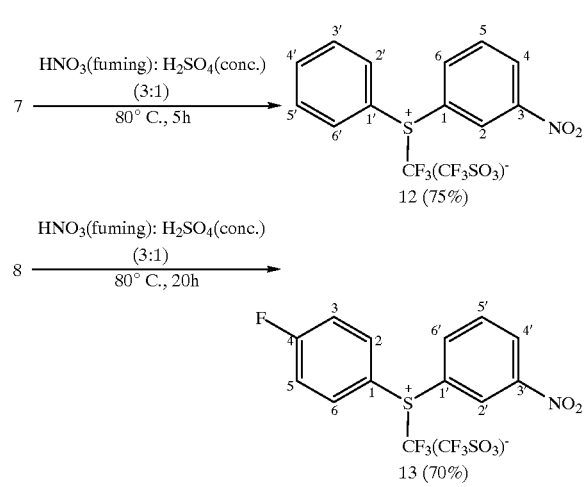

FIG. 10

Synthetic details S-(trifluoromethyl)phenyl 3 nitrophenylsulfonium triflate (12): To fuming nitric acid (0.12 mL, 2–5 mmol, 90%, d=1.5) was added concentrated $H_2SO_4$ (0.35 mL, d=1.98). After the mixture was stirred for one-half hour, S-(trifluoromethyl)diphenylsulfonium triflate (7) (1.0 g, 2.5 mmol) was added. The reaction mixture was stirred for 5 h .t 100° C., and then diethyl ether was slowly added to the mixture. The resulting pile yellow crystals were collected by filtration and recrystallized with $CH_3CN$—$CH_2Cl_2$ to give 833 mg (75%) of 12, m. p. 87–9° C. IR (nujol): 1450 (s), 1225 (s), 1589 (m), 1031 (s), 639 (s), 585 (s) $cm^{-1}$; $^1H$ NMR ($CDCl_3$): 8.83 (dd, $J_{24}=J_{26}$ 2.0 Hz, 1H), 8.75 (ddd, $J_{45}=6.0$ Hz, $J_{42}=J_{46}=2.0$ Hz, 1H), 8.42 (dm. $J_{65}=6.0$ Hz, 1H), 8.15 (m, 4H), 7.90 (m, 2H); $^{19}F$ NMR ($CDCl_3$): −48.1 (s, 3F), −78.3 (s, 3F); $^{13}C$ NMR ($CDCl_3$): 139, 138, 137, 136, 135, 134, 133, 132, 129, 123 (q, J=264 Hz), 122 (q, J=263 Hz), 117 ppm; $FAB^+$-MS [m/e (species, intensity)]: 300 (($C_{13}H_9F_3NO_2S)^+$, 100) ); Chemical analysis: Calculated for $C_{14}H_9F_6NO_5S_2$: C, 37.42; H. 2.02; N, 3.12. Found: C, 37.32; H, 1.98; N, 2.90.

Synthetic details-S-(trifluoromethyl)-4-fluorophenyl-3-nitrophenylsulfonium triflate (13): To fuming nitric acid (0.60 mL, 14.2 mmol, 90%, d=1.5) was added concentrated $H_2SO_4$ (2.0 mL, d=1.98). After the mixture was stirred for one-half hour, S-(trifluoromethyl)phenyl-4-fluorophenylsulfonium triflate (8) (2.0 g, 4.7 mmol) was added to the solution. The reaction mixture was stirred for 20 h at 100° C. Diethyl ether was slowly added to the mixture. The resulting pale yellow crystals were collected by filtration, and then recrystallized with $CH_3CN$—$CH_2Cl_2$ to give 1.5 g of 13 (70%), m. p. 87–8° C. IR (nujol): 3105 (m), 1588 (s), 1494 (m), 1450 (s), 1087 (s) $cm^{-1}$; $^1H$ NMR ($CDCl_3$): 8.81 (dd, $J_{2'4'}=J_{2'6'}=2.0$ Hz, 1H), 8.73 (ddd, $J_{4'5'}=$ 6.0 Hz, $J_{4'2'}J_{4'6'}=2.0$ Hz, 1H), 8.42 (dm, $J_{6'5'}=8.0$ Hz, 1H), 8.24 (dd, $J_{23}=8.0$ Hz, $J_{2F}=8.0$ Hz, 2H), 8.10 (dd, $J_{5'4'}=J_{5'6'}=$ 8.0 Hz, 1H), 7.67 (dd, $J_{32}=8.0$ Hz, $J_{3F}=8.1$ Hz, 2H); $^{19}F$ NMR ($CDCl_3$): −48.3 (s, 3F), −78.3 (s, 3F), −95.3 (s, 1F); $^{13}C$ NMR ($CDCl_3$): 170 (d, J=260 Hz), 152, 138, 137, 135, 132, 129, 127 (q, J=262 Hz), 121, 121, 120 (q, J=262 Hz), 116 ppm; $FAB^+$-MS [m/e (species, intensity)]: 318 (($C_{13}H_8F_4NO_2S)^+$, 100), 300 (($C_{13}H_8F_4NO_2S)^+$-F+H, 61.2), 272 (($C_{13}H_8F_4NO_2S)^+$-$NO_2$, 3.6), 250 (($C_{13}H_8F_4NO_2S)^+$-$CF_3$+H, 2.9) ); Chemical analysis: Calculated for $C_{14}H_8F_7NO_5S_2$: C, 35.98; H, 1.73; N, 3.00. Found: C, 35.74; H, 1.67; N, 2.92.

EXAMPLE 7

Preparation of S-(trifluoromethyl)phenyl-2-trifluoromethylthiophenylsulfonium Triflate (17)

S-(trifluoromethyl)phenyl-2-trifluoromethylthiophenylsulfonium triflate (17) was synthesized as shown in FIG. 11. 1,2-Diiodobenzene was converted to phenyl 1,2-bis(trifluoromethyl sulfide) (14) in 84% yield. Compound 14 was oxidized to phenyl 1,2-bis (trifluoromethyl sulfoxide) (15) under reflux. No sulfone was isolated with the only by-product being phenyl 2-trifluoromethylthio trifluoromethyl sulfoxide (16). It is likely that a bulk steric effect hindered further oxidation and the reaction stopped at the sulfoxide stage. Compound 15 reacted with benzene and $Tf_2O$ to give the product S-(trifluoromethyl)phenyl-2-trifluoromethylthiophenylsulfonium triflate (17).

FIG. 11

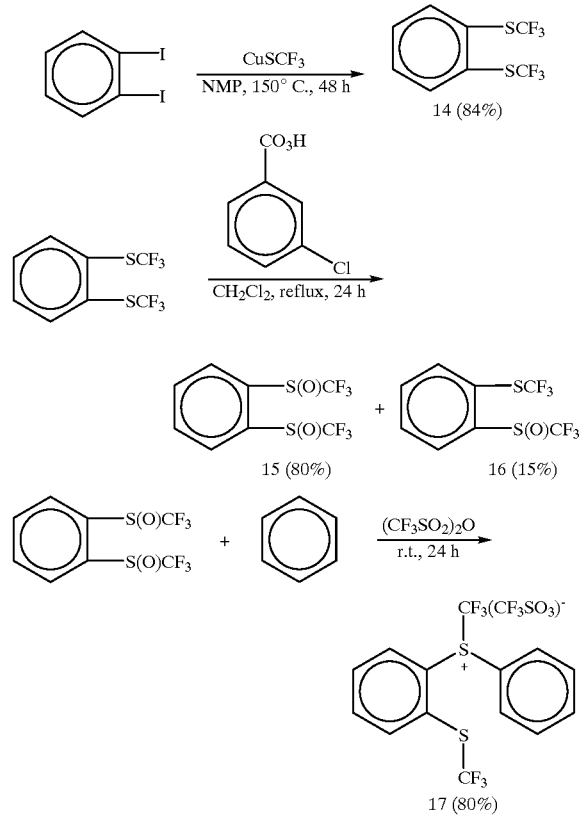

Synthetic details-Phenyl 1,2-bis(trifluoromethyl sulfide) (14): Trifluoromethylthiocopper (I) (9.0 g, 54.98 mmol), 1,2-diiodobenzene (2.6 g, 8.55 mmol) and NMP (N-methylpyrrolidone) (50 mL) were placed in a 100 mL round bottom flask and heated at 150° C. for 2 d. Water (30 mL) was then added and the organic products were extracted with diethyl ether (60 mL×3). The ether layer was washed with water (30 mL×3), and the ether was removed on a rotary evaporator to yield 3 g of product. The reaction mixture was purified by column chromatography by using ethyl acetate:hexanes=1:30 as eluent to give the pure product (2 g, 84%), mp 40° C. IR (Nujol): 3000 (w), 1457 (w), 1127 (s), 1101 (s), 1033 (s), 761 (s), 664 (m) (cm$^{-1}$); $^1$H NMR (CDCl$_3$): 7.85 (dd, J$_{34}$=6.0 Hz, J$_{35}$=4.0 Hz, 2H, H3 and H6), 7.52 (dd, J$_{43}$=6.0 Hz, J$_{46}$=4.0 Hz, 2H, H4 and H5); $^{19}$F NMR (CDCl$_3$): −42.10 (s, 3F, CF$_3$); $^{13}$C NMR (CDCl$_3$): 138.28 (C3, C6), 133.10 (C1, C2), 131.96 (C4, C5), 126.79 (q, J=314 Hz, CF$_3$) ppm; EI-MS [m/e (species, intensity)] 278 (M$^+$, 85), 259 (M$^+$-F, 3), 209 (M$^+$-CF$_3$, 45), 190 (M$^+$-CF$_3$-F, 10), 140 (M$^+$-2CF$_3$, 100), 108 (M$^+$-SCF$_3$-CF$_3$, 12), 69 (CF$_3$, 7.2).

Synthetic details--Phenyl 1,2-bis(trifluoromethyl sulfoxide) (15): Under an N$_2$ atmosphere, m-chloroperbenzoic acid (903 mg, 2.5 mmol) was added in small portions to a stirred solution of phenyl 1,2-bis (trifluoromethyl sulfide) (14) (500 mg, 1.8 mmol) in dry CH$_2$Cl$_2$ (20 mL) at rt. The reaction mixture was refluxed for 24 h, filtered, and evaporated. The residue was column chromatographed on silica gel by using a (1:30) mixture of ethyl acetate and hexanes as eluent to give products 15 (446.4 mg, 80%) and 16 (83.7 mg, 15%). For 15 mp 69° C. IR (Nujol): 3017 (w), 2319 (w), 1448 (m), 1101 (s), 1081 (s), 675 (m), 610 (m) (cm$^{-1}$); $^1$H NMR (CDCl$_3$): 8.30 (dd, J$_{34}$=8.9 Hz, J$_{35}$=2.5 Hz, 2H, H3 and H6), 7.95 (dd, J$_{43}$=9.0 Hz, J$_{46}$=3.0 Hz, 2H, H4 and H5); $^{19}$F NMR (CDCl$_3$): −72.71 (s, 3F, CF$_3$); $^{13}$C NMR (CDCl$_3$): 134.70 (C3, C6), 134.01 (C1, C2), 130.02 (q, J=187.5 Hz, SCF$_3$), 127.08 (C4, C5) ppm; EI-MS [m/e (species, intensity)] 311 (M$^+$+H, 15), 241 (M$^+$-CF$_3$, 100), 194 (M$^+$+H -SOCF$_3$, 5). Phenyl 2-trifluoromethylthio trifluoromethyl sulfoxide (16) (83.7 mg, 15%), mp 58° C. IR (Nujol): 3010 (w), 1515 (w), 1411 (m), 1201 (s), 1015 (m), 612(m), 515(m) (cm$^{-1}$); $^1$H NMR (CDCl$_3$): 8.19 (dd, J$_{65}$=7.4 Hz, J$_{64}$=2.2 Hz, 1H, H6), 7.80 (m, 3H, H3, H4 and H5); $^{19}$F NMR (CDCl$_3$): −42.41 (s, SCF$_3$), −72.61 (s, CF$_3$) ppm; EI-MS [m/e (species, intensity)] 294 (M$^+$, 20), 225 (M$^+$-CF$_3$, 100).

Synthetic details-S-(trifluoromethyl)phenyl-2-trifluoromethylthiosulfonium triflate (17): To the solution of phenyl 1,2-bis(trifluoromethyl sulfoxide) (15) (200 mg, 0.625 mmol) in dry benzene (2 mL) was added (CF$_3$SO$_2$)$_2$O (0.6 mL, 3.2 mmol) at 0° C. The resulting solution was stirred at 0° C. for 1 h, and then at rt for an additional 24 h. The solution was evaporated and then purified by column chromatography on silica gel by using CH$_3$CN in CH$_2$Cl$_2$ (1:1) as eluent. The product was obtained as a yellow thick oil. (130 mg, 80%). IR (Nujol): 3100 (w), 1510 (w), 1500 (s), 1420 (m), 1100 (s), 610 (m) (cm$^{-1}$); $^1$H NMR (CDCl$_3$): 8.28 (m, 4H), 7.96 (m, 5H); $^{19}$F NMR (CDCl$_3$): −40.72 (s, 3F, SCF$_3$), −49.71 (s, 3F, $^+$SCF$_3$), −78.29 (s, 3F, CF$_3$SO$_3$); $^{13}$C NMR (CDCl$_3$): 137.60, 136.43, 136.43, 133.59, 133.40, 132.49, 132.23 (q, J=151 Hz, SCF$_3$), 131.71, 126.41, 124.12 (q, J=121 Hz, SCF$_3$), 119.90, 119.40, 117.43, 116.05, 112.13 (q, J=132 Hz, CF$_3$SO$_3$) ppm; FAB-MS [m/e (species, intensity)] 355 (M$^+$, 100).

EXAMPLE 8

Preparation of 1,4-Di-S-(trifluoromethyl) phenyldiphenylsulfonium Triflate (20)

The trifluoromethylating reagent 1,4-di-S-(trifluoromethyl)phenyldiphenylsulfonium triflate (20) was synthesized as shown in FIG. 12. For compound (19), regardless of the conditions used, it is difficult to find an ideal oxidant. Invariably a series of sulfide, sulfoxide and sulfone mixtures were isolated. When F-TEDA-BF$_4$ [1-chloromethyl-4-fluoro-1,4-diazoniabicyclo[2,2,2]octane bis(tetrafluoroborate)]was utilized under reflux, phenyl 1,4-bis(trifluoromethyl sulfoxide) (19) was isolated in high yield.

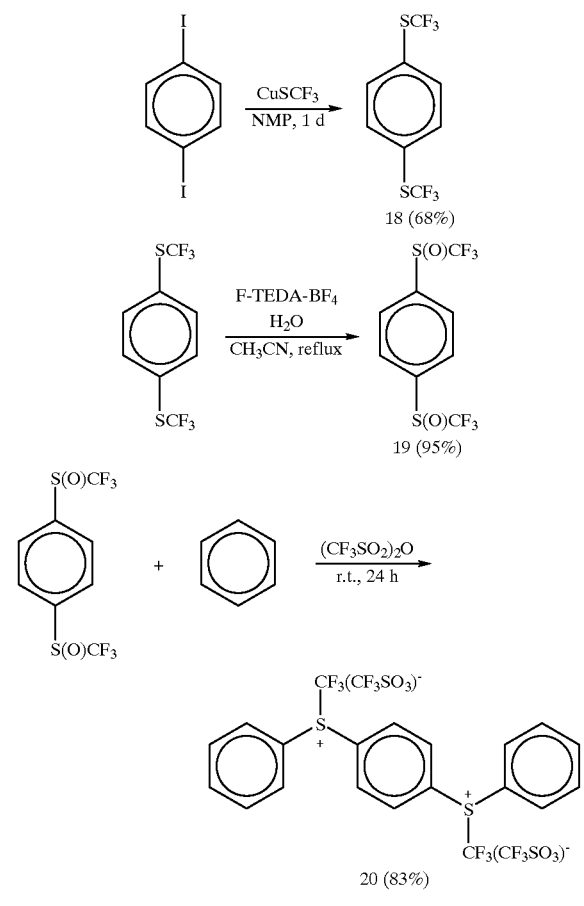

FIG. 12

Synthetic details-Preparation of Phenyl 1,4-bis (trifluoromethyl sulfide) (18): Trifluoromethylthiocopper (I) (9.9 g, 60 mmol), 1,4-diiodobenzene (3.3 g, 10 mmol) and NMP (N-methylpyrrolidone) (50 mL) were placed in a 100 mL round bottom flask and heated at 150° C. for 1 d. Water (30 mL) was then added and the organic products were extracted with diethyl ether (60 mL×3). The ether layer were washed with water (30 mL×3), and the ether was removed on a rotary evaporator to yield 3 g of product. The reaction mixture was purified by using column chromatography with ethyl acetate:hexanes=1:30 as the eluent. The product was recrystallized from ethyl acetate:hexanes as white crystals (1.88 g, 68%). mp 43° C. IR (Nujol): 3015(w), 2341 (m), 1457 (w), 1127 (s), 1101 (s), 1051 (s), 871 (s), 752 (m) (cm$^{-1}$); $^1$H NMR (CDCl$_3$): 7.56 (s, 4H, H2, H3, H5 and H6); $^{19}$F NMR (CDCl$_3$): −43.17 (s, 3F, CF$_3$); $^{13}$C NMR (CDCl$_3$): 139.27 (C1, C4), 136.41 (C2, C3, C5 and C6), 130.20 (q, J=318 Hz, CF$_3$) ppm; EI-MS [m/e (species, intensity)] 278 (M$^+$, 100), 259 (M$^+$-F, 5), 209 (M$^+$-CF$_3$, 90), 190 (M+-CF$_3$-F, 10), 140 (M$^+$-2CF$_3$, 30), 108 (M$^+$-SCF$_3$-CF$_3$, 10).

Synthetic details-Preparation of Phenyl 1,4-bis (trifluoromethylsulfoxide) (19): A solution of phenyl 1,4-bis (trifluoromethyl sulfide) (18) (360 mg, 1.3 mmol) in CH$_3$CN (20 mL) containing H$_2$O (2 mL) was treated with F-TEDA-BF$_4$ (1.38 g, 3.9 mmol) and refluxed for 24 h under N$_2$. On cooling, the solution was poured into diethyl ether (50 mL), washed with water (25 mL×2) and saturated NaHCO$_3$ (25 mL), dried (Na$_2$SO$_4$), filtered and evaporated in vacuo. Chromatography on silica gel in ethyl acetate:hexanes (1:4; 1:1) afforded (19) (382.9 mg, 95%). mp 75° C . IR (Nujol): 3009 (w), 2412 (w), 1310 (m), 1360 (m), 1101 (s), 658 (m), 601 (m) (cm$^{-1}$); $^1$H NMR (CDCl$_3$): 8.03 (s, 4H, H2, H3, H5 and H6); $^{19}$F NMR (CDCl$_3$): −73.40 (s, 6F, CF$_3$); $^{13}$C NMR (CDCl$_3$): 141.81 (C1, C4), 126.92 (C2, C3, C5 and C6), 123.5 (q, J=318 Hz, SCF$_3$) ppm; EI-MS [m/e (species, intensity)] 310 (M$^+$, 20), 241 (M$^+$-CF$_3$, 100), 193 (M$^+$-SOCF$_3$, 25).

Synthetic details-Preparation of 1,4-Di-S-(trifluoromethyl)phenyldiphenylsulfonium triflate (20): To the solution of phenyl 1,4-bis(trifluoromethyl sulfoxide) (19) (1.7 g, 5.48 mmol) in dry benzene (14 mL) was added (CF$_3$SO$_2$)$_2$O (4.6 mL, 27.4 mmol) at 0° C. The resulting solution was stirred at 0° C. for 1 h, and then at rt for 24 h. The solution was evaporated and purified by column chromatography on silica gel using a CH$_3$CN in CH$_2$Cl$_2$ (1:1) as eluent. The product was obtained as thick yellow oil (1.97 g, 83%). IR (Nujol): 3000 (w), 1480 (w), 1300 (s), 1111 (s), 1009 (s), 670 (m), 595 (m) (cm$^{-1}$); $^1$H NMR (CDCl$_3$): 8.0 (m, 14H); $^{19}$F NMR (CDCl$_3$): −49.12 (s, 6F, SCF$_3$), −78.73 (s, 6F, CF$_3$SO$_3$); $^{13}$C NMR (CDCl$_3$): 142.28, 138.64, 138.35, 137.01 (q, J=110 Hz, SCF$_3$), 126.04 (q, J=120 Hz, CF$_3$SO$_3$), 135.35, 134.00, 133.33 ppm; FAB-MS [m/e (species, intensity)] 363 (M$^+$-CF$_3$, 20), 355 (M$^+$-C$_6$H$_5$, 100).

Preparation of Trifluoromethylating Reagents-Summary

Nine trifluoromethylating reagents, as shown in FIG. 13, have been disclosed.

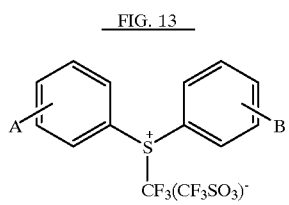

FIG. 13

| Cpd. No. | 7 | 8 | 9 | 10 | 11 | 12 | 13 | 17 | 20 |
|---|---|---|---|---|---|---|---|---|---|
| A = | H | H | H | H | H | H | F | H | H |
| B = | H | F | F,F | OCF$_3$ | OCHF$_2$ | NO$_2$ | NO$_2$ | SCF$_3$ | S$^+$(CF$_3$)C$_6$H$_5$ |

B. Trifluoromethylating Reactions

The ability of the reagents of the present invention to transfer CF$_3$ to different substrates was demonstrated. Relative amounts of products formed were determined based on $^{19}$F NMR spectral analysis. Because of the electron-withdrawing properties of the nitro group on the benzene ring, compounds 12 and 13 are more effective transfer reagents than 7, 8, 17, and 20. When there are two fluorine atoms on the benzene ring, the electrophilic trifluoromethylating ability of the sulfonium triflate is enhanced. Thus 9 is also more reactive than either 7, 8, 10, 11, 17or 20.

The general method for the trifluoromethylation reactions is as follows: To a stirred solution of 0.8–4.0 mmol of substrate in 10 mL of dry THF under N$_2$ was added 1 mmol of a trifluoromethyl onium salt. Detailed conditions are shown in Tables 2, 3, 4, 5, 6, 7, 8and 9. After the reaction was complete, the reaction mixture was studied by $^1$H and $^{19}$F NMR. In $^{19}$F NMR, the triflate anion of the trifluoromethyl onium triflate was used as an internal standard to determine the yield of product.

EXAMPLE 9

Trifluoromethylation of p-hydroquinone p-Hydroquinone was trifluoromethylated with reagents 7–13, 17 and 20 in the presence of pyridine as a base, as illustrated in Table 2. Yields of 2-trifluoromethyl-p-hydroquinone obtained were determined by $^{19}$F NMR and $^1$H NMR spectral analysis. At rt, the abilities of 12 and 13 to transfer CF$_3$ appeared about equal. At higher temperatures, 9 functioned very effectively as an electrophilic trifluoromethylating reagent, but increase in temperature did not impact the ability of the reagents 7 and 8 to transfer CF$_3$.

TABLE 2

Trifluoromethylation of p-hydroquinone by various trifluoromethylating reagents

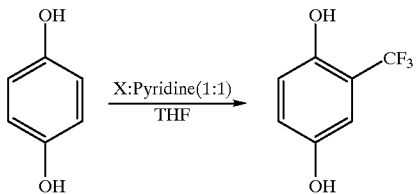

| X | Molar ratio* | Condition | Yield** |
|---|---|---|---|
| 7 | 2:1 | rt, 5 h | 5% |
| 10 | 2:1 | rt, 5 h | 10% |
| 11 | 2:1 | rt, 5 h | 9% |
| 12 | 2:1 | rt, 5 h | 40% |
| 8 | 2:1 | rt, 5 h | 6% |
| 13 | 2:1 | rt, 5 h | 40% |
| 9 | 2:1 | rt, 5 h | 10% |
| 9 | 2:1 | reflux, 10 h | 85% |
| 17 | 2:1 | rt, 5 h | 5% |
| 17 | 2:1 | reflux, 10 h | 30% |
| 20 | 4:1 | rt, 5 h | 5% |
| 20 | 4:1 | reflux, 10 h | 30% |

*molar ratio = substrate:CF$_3^+$
**Yields determined from $^{19}$F NMR spectra.

EXAMPLE 10

Trifluoromethylation of Pyrrole

Trifluoromethylation of pyrrole is shown in Table 3. 2-Trifluoromethylpyrrole was the product of trifluoromethylation of pyrrole under reflux conditions. No products containing more than one CF$_3$ group were isolated. When the reactions were carried out at room temperature, the yields were low, e.g., for compounds 7 and 8, only starting material was recovered, and for compounds 9, 10, 11, 12 and 13, the yields were less than 10%. However, under reflux, 9, 12, 13, 17 and 20 gave yields of 2-trifluoromethylpyrrole of 80% or better. With 9, 17 and 20 a longer reflux time was required. p-Hydroquinone is more electron-rich than pyrrole, and consequently its reactivity is higher as demonstrated by the fact that transfer of CF$_3$ takes place readily at room temperature.

TABLE 3

Trifluoromethylation of pyrrole by various trifluoromethylating agents

| X | Molar ratio* | Condition | Yield** |
|---|---|---|---|
| 7 | 1:2.5 | reflux, 2 h | 6% |
| 10 | 1:2.5 | reflux, 2 h | 10% |
| 11 | 1:2.5 | reflux, 2 h | 8% |
| 12 | 1:2.5 | reflux, 2 h | 80% |
| 8 | 1:2.5 | reflux, 2 h | 10% |
| 13 | 1:2.5 | reflux, 2 h | 85% |
| 9 | 1:2.5 | reflux, 2 h | 50% |
| 9 | 1:2.5 | reflux, 10 h | 87% |
| 17 | 1:2.5 | reflux, 2 h | 40% |
| 17 | 1:2.5 | reflux, 10 h | 80% |
| 20 | 1:1.25 | reflux, 2 h | 35% |
| 20 | 1:1.25 | reflux, 10 h | 80% |

*molar ratio = substrate:$CF_3^+$
**Yields determined from $^{19}F$ NMR spectra.

EXAMPLE 11

Trifluoromethylation of Aniline

Trifluoromethylation of aniline is shown in Table 4. Two products were identified when treating aniline with reagents 7–13, 17 and 20 in THF at reflux. When the reactions were carried out at room temperature, only starting materials were obtained.

TABLE 4

Trifluoromethylation of aniline by various trifluoromethylating reagents

| X | Molar ratio* | Condition | Yield**(21:22) |
|---|---|---|---|
| 7 | 1:2 | reflux, 10 h | trace, trace |
| 10 | 1:2 | reflux, 10 h | trace, trace |
| 11 | 1:2 | reflux, 10 h | trace, trace |
| 12 | 1:2 | reflux, 10 h | 70%, 18% |
| 8 | 1:2 | reflux, 10 h | trace, trace |
| 13 | 1:2 | reflux, 10 h | 66%, 17% |
| 9 | 1:2 | reflux, 10 h | 33%, 31% |
| 17 | 1:2 | reflux, 10 h | 52%, 18% |
| 20 | 1:1 | reflux, 10 h | 52%, 18% |

*molar ratio = substrate:$CF_3^+$
**Yields determined from $^{19}F$ NMR spectra.

EXAMPLE 12

Trifluoromethylation of 1,3-dimethoxybenzene 1,3-Dimethoxybenzene was trifluoromethylated with reagents 7–13, 17 and 20 in the presence of pyridine as a base as shown in Table 5, together with the yields of 2,4-dimethoxy-1-trifluoromethyl benzene which were obtained. At reflux condition, compounds 9 and 13 are more reactive than other reagents.

TABLE 5

Trifluoromethylation of 1,3-dimethoxybenzene by various trifluoromethylating agents

| X | Molar ratio* | Condition | Yield** |
|---|---|---|---|
| 7 | 2:1 | reflux, 10 h | 10% |
| 10 | 2:1 | reflux, 10 h | 12% |
| 11 | 2:1 | reflux, 10 h | 14% |
| 12 | 2:1 | reflux, 10 h | 65% |
| 8 | 2:1 | reflux, 10 h | 8% |
| 13 | 2:1 | reflux, 10 h | 75% |
| 9 | 2:1 | reflux, 10 h | 85% |
| 17 | 2:1 | reflux, 10 h | 42% |
| 20 | 4:1 | reflux, 10 h | 45% |

*molar ratio = substrate:$CF_3^+$
**Yields determined from $^{19}F$ NMR spectra.

EXAMPLE 13

Trifluoromethylation of 1-pyrrolidino-1-cyclohexene

The transfer reagents of the present invention were tested with 1-pyrrolidino-1-cyclohexene to give 2-trifluoromethyl cyclohexanone. The yields varied from 7% to 80%. Reagents 9 and 13 are better transfer reagents than are the others under the two sets of reaction conditions.

TABLE 6

Trifluoromethylation of 1-pyrrolidino-1-cyclohexene by various trifluoromethylating agents

| X | Molar ratio* | Condition | Yield** |
|---|---|---|---|
| 7 | 2:1 | 0° C., 2 h | 7% |
| 10 | 2:1 | 0° C., 2 h | 10% |
| 11 | 2:1 | 0° C., 2 h | 10% |
| 12 | 2:1 | 0° C., 2 h | 33% |
| 12 | 2:1 | 0° C., 10 h | 62% |
| 8 | 2:1 | 0° C., 2 h | 7% |
| 13 | 2:1 | 0° C., 2 h | 30% |
| 13 | 2:1 | 0° C., 10 h | 78% |
| 9 | 2:1 | 0° C., 2 h | 20% |
| 9 | 2:1 | 0° C., 10 h | 80% |
| 17 | 2:1 | 0° C., 2 h | 20% |
| 17 | 2:1 | 0° C., 10 h | 52% |
| 20 | 4:1 | 0° C., 2 h | 22% |

TABLE 6-continued

Trifluoromethylation of 1-pyrrolidino-1-cyclohexene by various trifluoromethylating agents

| X | Molar ratio* | Condition | Yield** |
|---|---|---|---|
| 20 | 4:1 | 0° C., 10 h | 49% |

*molar ratio = substrate:$CF_3^+$
**Yields determined from $^{19}F$ NMR spectra.

EXAMPLE 14

Trifluoromethylation of 2-naphthol

All of the reagents also were tested with 2-naphthol to prepare 1-trifluoromethyl-2-naphthol. Overall 9 and 13 are the best transfer reagents. The converted yields of compounds 9, 12, 13, 17 and 20 can be increased by using longer reaction time.

TABLE 7

Trifluoromethylation of 2-naphthol by various trifluoromethylating agents

| X | Molar ratio* | Condition | Yield** |
|---|---|---|---|
| 7 | 2:1 | −20° C. → rt, 2 h | 10% |
| 10 | 2:1 | −20° C. → rt, 2 h | 12% |
| 11 | 2:1 | −20° C. → rt, 2 h | 14% |
| 12 | 2:1 | −20° C. → rt, 2 h | 29% |
| 12 | 2:1 | −20° C. → rt, 10 h | 59% |
| 8 | 2:1 | −20° C. → rt, 2 h | 8% |
| 13 | 2:1 | −20° C. → rt, 2 h | 33% |
| 13 | 2:1 | −20° C. → rt, 10 h | 74% |
| 9 | 2:1 | −20° C. → rt, 2 h | 30% |
| 9 | 2:1 | −20° C. → rt, 10 h | 85% |
| 17 | 2:1 | −20° C. → rt, 2 h | 24% |
| 17 | 2:1 | −20° C. → rt, 10 h | 57% |
| 20 | 4:1 | −20° C. → rt, 2 h | 27% |
| 20 | 4:1 | −20° C. → rt, 10 h | 58% |

*molar ratio = substrate:$CF_3^+$
**Yields determined from $^{19}F$ NMR spectra.

EXAMPLE 15

Trifluoromethylation of Uracil

Six of the reagents also were tested with uracil to prepare 5-trifluoromethyluracil. Overall 12 and 13 are the best transfer reagents.

TABLE 8

Trifluoromethylation of uracil by various trifluoromethylating agents

| X | Molar ratio* | Condition | Yield** |
|---|---|---|---|
| 8 | 1:1 | 90° C., 2 h | 30% |
| 9 | 1:1 | 90° C., 2 h | 40% |
| 12 | 1:1 | 90° C., 2 h | 47% |
| 13 | 1:1 | 90° C., 2 h | 56% |
| 17 | 1:1 | 90° C., 2 h | 40% |
| 20 | 1:1 | 90° C., 2 h | 42% |

*Molar ratio = substrate:$CF_3^+$
**Yields determined from $^{19}F$ NMR spectra.

EXAMPLE 16

Trifluoromethylation with S-(trifluoromethyl)-4-fluorophenyl-3-nitrophenylsulfonium triflate (13)

The breadth of the one of these compounds (13) is demonstrated by the additional data recorded in Table 9. Prior to reaction with 13, the reactivity of several of the compounds has been enhanced by converting the substrate into its carbanion as shown in runs 1–8. A similar behavior is expected for each of the other eight trifluoromethylating reagents.

TABLE 9

Trifluoromethylation reactions of trifluoromethylating agent (13)

| Run | Substrate | Molar ratio* | Condition | Product | Yield** |
|---|---|---|---|---|---|
| 1 | phenylacetylene | 1:1.2 | n-$C_4H_9$Li/THF $-78°$ C. to r.t. 5 h | 1-$CF_3$-phenylacetylene | 62% |
| 2 | ethyl-2-oxocyclopen-tane carboxylate | 1:1.2 | NaH (85% in oil) THF $-50°$ C. to r.t. 7 h | 1-$CF_3$-ethyl-2-oxocyclopentane carboxylate | 70% |
| 3 | 2-methyl-1,3-cyclopentanedione | 1:1.2 | NaH (85% in oil) THF $-50°$ C. to r.t. 7 h | 1-$CF_3$-2-methyl-1,3-cyclopentanedione | 78% |
| 4 | diethyl methyl malonate | 1:1.2 | NaH (85% in oil) THF $-50°$ C. to r.t. 7 h | 1-$CF_3$-diethyl methyl malonate | 45% |
| 5 | 2-methyl-1-indanone | 1:1.2 | n-$C_4H_9$Li/THF $-78°$ C. to r.t. 5 h | 1-$CF_3$-2-methyl-1-indanone | 58% |
| 6 | ethyl benzol acetate | 1:1.2 | NaH (85% in oil) THF $-50°$ C. to r.t. 7 h | 1-$CF_3$-2-ethyl benzol acetate | 47% |
| 7 | dibenzoyl methane | 1:1.2 | NaH (85% in oil) THF $-50°$ C. to r.t. 7 h | 1-$CF_3$-dibenzoyl methane | 52% |
| 8 | diethyl phenyl malonate | 1:1.2 | NaH (85% in oil) THF $-50°$ C. to r.t. 7 h | 1-$CF_3$-diethyl phenylmalonate | 44% |
| 9 | uridine | 1:1.2 | DMF, $90°$ C., 12 h | 1-$CF_3$-uridine | 47% |
| 10 | D-glucal | 1:1.2 | DMF, $80°$ C., 12 h | 1-$CF_3$-D-glucal | 30% |
| 11 | cytidine | 1:1.2 | DMF $90°$ C., 12 h | 1-$CF_3$-cytidine | 49% |
| 12 | 3,4-di-o-acetyl-L-glucal | 1:1.2 | DMF, $80°$ C., 12 h | 1-$CF_3$-3,4-di-o-acetyl-L-glucal | 35% |

*molar ratio = substrate:$CF_3^+$
**Yields determined from $^{19}F$ NMR spectra.

We have demonstrated that aromatic ring substituted S-(trifluoromethyl)diphenylsulfonium triflates react with aryl, cyclohexene, pyrimidine, and nucleotide substrates to give compounds that contain the trifluoromethyl group. In some cases, reactivity of the substrate is enhanced by preforming the respective carbanion. The electrophilic trifluoromethylating reagents that we have described are thermally and hydrolytically stable molecules, and are inexpensive and convenient to prepare. Their electrophilic trifluoromethylating potential can be altered by changing the substitutents on the benzene rings. When electron-withdrawing groups ($NO_2$, F) were present on the benzene ring, transfer of the $CF_3$ group to electron-rich substrates was enhanced.

As is evident from Tables 2 through 9, the relative efficacy of the reagents of the invention in transferring a trifluoromethyl group varies with the target molecule. In general, however, the difluoro-substituted compound 9, S-(trifluoromethyl)phenyl-2,4-difluorophenylsulfonium triflate, was the most effective reagent in most cases, although the nitro-, and nitro- and monofluoro-substituted compounds 12 and 13, S-(trifluoromethyl)phenyl-3-nitrophenylsulfonium triflate and S-(trifluoromethyl)-4-fluorophenyl-3-nitrophenylsulfonium triflate, respectively, were somewhat more effective when uracil and aniline were the targets. In these cases, the S-(trifluoromethyl)phenyl-2,4-difluorophenylsulfonium triflate (9) was almost as effective.

The preceding descriptions of the various embodiments of the invention should not be taken as limiting the scope of the invention, which will be determined from the claims.

What is claimed is:

1. A composition of matter, comprising a compound having the formula:

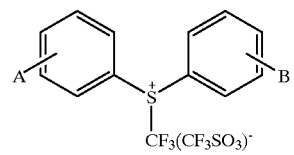

wherein A comprises H or F and B comprises F, $SCF_3$, $OCF_3$, $OCHF_2$, $S^+(CF_3)C_6H_5$, or $NO_2$.

2. The composition of claim 1, wherein A comprises H and B comprises F, $SCF_3$, $OCF_3$, $OCHF_2$, $S^+(CF_3)C_6H_5$, or $NO_2$.

3. The composition of claim 1, wherein A comprises H and B comprises F.

4. The composition of claim 1, wherein A comprises H and B comprises $SCF_3$.

5. The composition of claim 1, wherein A comprises H and B comprises $OCF_3$.

6. The composition of claim 1, wherein A comprises H and B comprises $OCHF_2$.

7. The composition of claim 1, wherein A comprises H and B comprises $S^+(CF_3)C_6H_5$.

8. The composition of claim 1, wherein A comprises H and B comprises $NO_2$.

9. The composition of claim 1, wherein A comprises F and B comprises $NO_2$.

10. A composition of matter, comprising a compound having the formula:

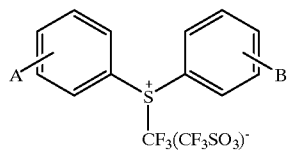

wherein A comprises F and B comprises H.

11. A process for preparing a trifluoromethyl diphenyl-sulfonium triflate compound corresponding to the formula:

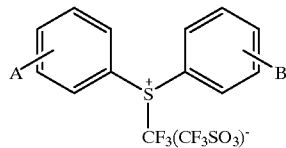

comprising reacting phenyl trifluoromethyl sulfoxide or one of its derivatives with an aromatic compound, wherein A comprises H or F and B comprises F, $SCF_3$, $OCF_3$, $OCHF_2$, $S^+(CF_3)C_6H_5$, or $NO_2$.

12. The process of claim 1, wherein the aromatic compound comprises benzene, a fluorine containing benzene, trifluoromethoxy benzene, or αα difluoranisol.

13. The process of claim 11, wherein the step of reacting comprises reacting an aromatic compound with phenyl trifluoromethyl sulfoxide or one of its derivatives in the presence of triflic anhydride.

14. A process for preparing a trifluoromethyl diphenyl-sulfonium triflate compound corresponding to the formula:

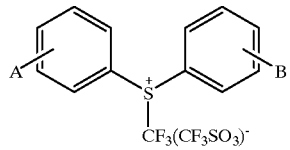

comprising reacting a trifluoromethyl diphenylsulfonium triflate with a mixture of fuming nitric acid and sulfuric acid, wherein A is H or F and B is $NO_2$.

15. A process for preparing a trifluoromethyl diphenyl-sulfonium triflate compound corresponding to the formula:

comprising reacting a trifluoromethyl phenyl-4-fluorophenylsulfonium triflate with a mixture of fuming nitric acid and sulfuric acid, wherein A is F and B is $NO_2$.

16. A process for preparing a trifluoromethyl diphenyl-sulfonium triflate compound corresponding to the formula:

comprising inducing a reaction of phenyl trifluoromethyl sulfoxide or one of its derivatives and an aromatic compound.

17. The process of claim 16, wherein the aromatic compound comprises benzene or a fluorine containing benzene.

18. The process of claim 16, comprising inducing a reaction of phenyl trifluoromethyl sulfoxide or one of its derivatives and an aromatic compound by the action of trifluoromethanesulfonic anhydride.

19. The process of claim 16, comprising inducing a reaction of phenyl trifluoromethyl sulfoxide or one of its derivatives and an aromatic compound by the action of trifluoromethanesulfonic anhydride at room temperature.

* * * * *